US010813590B2

(12) United States Patent
Ruppersberg

(10) Patent No.: US 10,813,590 B2
(45) Date of Patent: Oct. 27, 2020

(54) ELECTROPHYSIOLOGICAL MAPPING CATHETER

(71) Applicant: Ablacon Inc., Wheat Ridge, CO (US)

(72) Inventor: Peter Ruppersberg, Blonay (CH)

(73) Assignee: Ablacon Inc., Wheat Ridge, CO (US)

( * ) Notice: Subject to any disclaimer, the term of this patent is extended or adjusted under 35 U.S.C. 154(b) by 240 days.

(21) Appl. No.: 15/793,594

(22) Filed: Oct. 25, 2017

(65) Prior Publication Data

US 2018/0116595 A1 May 3, 2018

Related U.S. Application Data

(60) Provisional application No. 62/414,183, filed on Oct. 28, 2016.

(51) Int. Cl.
*A61B 5/00* (2006.01)
*A61B 5/042* (2006.01)

(52) U.S. Cl.
CPC .......... *A61B 5/6858* (2013.01); *A61B 5/0422* (2013.01); *A61B 2562/0209* (2013.01); *A61B 2562/046* (2013.01); *A61B 2562/125* (2013.01); *A61B 2562/164* (2013.01)

(58) Field of Classification Search
CPC .............. A61B 5/6858; A61B 5/0422; A61B 2562/0209; A61B 2562/125; A61B 2562/164; A61B 2562/046
See application file for complete search history.

(56) References Cited

U.S. PATENT DOCUMENTS

| 10,362,952 | B2 * | 7/2019 | Basu | A61B 5/6858 |
|---|---|---|---|---|
| 10,362,953 | B2 * | 7/2019 | Basu | A61B 5/6858 |
| 2012/0271135 | A1 * | 10/2012 | Burke | A61B 5/0422 600/373 |
| 2015/0105645 | A1 * | 4/2015 | Subramaniam | A61B 5/6859 600/374 |
| 2015/0250424 | A1 * | 9/2015 | Govari | A61B 5/6858 600/373 |
| 2017/0035497 | A1 * | 2/2017 | Nagale | A61B 18/1492 |

\* cited by examiner

*Primary Examiner* — Linda C Dvorak
*Assistant Examiner* — Rachel A. Vierra
(74) *Attorney, Agent, or Firm* — Woods Patent Law, P.C.

(57) ABSTRACT

Disclosed are various examples and embodiments of a cardiac mapping catheter configured for electrophysiological (EP) mapping and suitable for intravascular insertion in a patient's heart, and methods of making same. The cardiac mapping catheter comprises a plurality support arms having electrodes disposed thereon. Various configurations of the cardiac mapping catheter are described and disclosed which provide improved spatial resolution and sensing of EP signals acquired from inside a patient's heart.

19 Claims, 6 Drawing Sheets

ELECTROPHYSIOLOGICAL MAPPING CATHETER

RELATED APPLICATIONS

This application claims priority and other benefits from U.S. Provisional Patent Application Ser. No. 62/414,183 entitled "Improved Electrophysiological Mapping Catheter" to Ruppersberg filed Oct. 28, 2016 (hereafter "the '183 patent application"). The entirety of the '183 patent application is hereby incorporated by reference herein.

FIELD OF THE INVENTION

Various embodiments described and disclosed herein relate to the field of medicine generally, and more particularly to electrophysiological (EP) mapping catheters employed to diagnose and treat cardiac rhythm disorders in a patient's heart.

BACKGROUND

Elongated medical devices suitable for intravascular insertion, such as catheters, especially ablation catheters, and guide wires for guiding catheters through vessels, organs or other body cavities are often employed in the treatment of atrial fibrillation (Afib). Atrial fibrillation is the most frequent arrhythmic disorder of the heart. Blood clotting occurring in the fibrillating atria is one main cause of stroke. Afib is also one of the most important disorders associated with a high risk of fatality. The cause of Afib has been subject to intensive scientific investigations and is largely understood. In most patients, the pulmonary veins draining into the left atrium are the sources of rapid arrhythmic action potentials which trigger circular excitation patterns (rotors) in the left atrium that induce a high frequency fibrillation through their re-entry mechanism. Those rotors have the character of small action potential cyclones of 2 to 3 $cm^2$ in size. The likelihood of occurrence of those rotors and the frequency of pathological action potential generation in the pulmonary veins increases with fibrotic structural changes and certain modifications of ion channel expression patterns in atrial cells with age.

The only potentially curative treatments for Afib are open heart surgery or cardiac ablation employing a catheter for those parts of the atrial wall tissue which originate, transmit or maintain the pathologic excitation circles.

Open heart surgery and catheter ablation are limited by potentially fatal and/or severe side effects associated with either procedure. When the integrity of the atrial wall is destroyed by excessive ablation, perforations of the atrial wall into the pericardium or fistulas into the esophagus can result in severe to deadly outcomes. The alteration of endocardial cells on the intra-cardiac surfaces can also initiate clotting in the treated atrium, which may lead to deadly strokes. That is why ablation procedures require the use of anticoagulation techniques. Last but not least, if the intensity of the ablation is kept too low to avoid the foregoing side effects, in many cases the therapeutic effect is insufficient and patients are often provided with success rates of only 50-70%.

To improve the situation, mapping catheters are often used first to identify circular excitation patterns (rotors) in the left atrium. After rotors have been identified, force sensing catheters are used that allow improved control of cardiac ablation catheter positions and pressures, which permits the intensity of tissue ablation to be better modulated and controlled. Further, water irrigation is often employed to keep endothelial tissue free of lesions during the ablation procedure, and micro-calorimetric sensors may be employed to measure and control the amount of heat delivered to the tissue during the ablation procedure.

U.S. Pat. No. 8,364,234 discloses a system for sensing multiple local electric voltages from endocardial surface of a heart. The system includes a first elongate tubular member; a basket assembly having a plurality of flexible splines for guiding a plurality of exposed electrodes, the splines having proximal portions, distal portions and medial portions therein between; a proximal anchor for securely affixing the proximal portions of the splines; the proximal anchor being secured at the distal end of the first elongate tubular member; a distal tip consisting essentially of means for only securely affixing the distal portions of the splines wherein at least some of the splines in the radially expanded non-spherical shape contain a distal outward bend disposed at the distal portion of the spline at a location near to the distal tip of the basket assembly to bend the splines back towards the proximal anchor. A disadvantage of this type of mapping system is the low resolution sometimes provided by the mapping electrode array, as the splines upon which the electrodes are mounted or attached tend to bunch or cluster when the endocardial surface of the patient's heart is contacted, thus reducing the area of the patient's heart that is sensed, and the spatial resolution provided, by the electrodes.

Laughner et. al. in JACC, CLINICAL ELECTROPHYSIOLOGY, 2016; 2(1):55-65. doi: 10.1016, conclude that known mapping basket catheters (MBC's) provide insufficient spatial resolution due to poor contact, demonstrate frequent bunching of basket splines, and possess inadequate electrode density to permit accurate detection of rotors near the equatorial electrodes of MBCs.

What is needed are improved means and methods of acquiring cardiac mapping data from inside a patient's heart using a cardiac mapping catheter, where improved spatial resolution of the electrodes when they are in contact with the patient's endocardium is provided.

SUMMARY

In one embodiment, there is provided a cardiac mapping catheter configured for electrophysiological mapping and suitable for intravascular insertion in a patient's heart comprising a flexible elongated body having a distal portion with a distal end and a proximal portion and an electrode assembly located at the distal portion, the electrode assembly comprising a plurality x of at least 4 support arms, each support arm having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition where the plurality of support arms is arranged in a collapsed bundle, and a second expanded condition where the plurality of support arms forms an expanded basket structure, wherein the plurality of support arms further comprises first and second neighboring support arms, the proximal end parts of the first and second neighboring support arms being combined or held together near or adjoining one another, the distal end part of the first support arm being combined or held together near or adjoining a distal end part of a neighboring support arm that is not the second support arm, the distal end part of the second support arm being combined or held together near or adjoining a distal end part of a neighboring support arm that is not the first support arm, each of the plurality of support arms in the electrode assembly being combined or held together at or near its distal end part with a neighboring support arm that is different from the neighboring support arm with which it is combined or held together at its proximal end part.

In another embodiment, there is provided a method of making a cardiac mapping catheter configured for electrophysiological mapping and suitable for intravascular insertion in a patient's heart, the method comprising forming a flexible elongated body having a distal portion with a distal end and a proximal portion, and forming an electrode assembly configured to be located at or near the distal portion, the electrode assembly comprising a plurality x of at least 4 support arms, each support arm having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition where the plurality of support arms is arranged in a collapsed bundle, and a second expanded condition where the plurality of support arms forms an expanded basket structure, wherein the plurality of support arms further comprises first and second neighboring support arms, the proximal end parts of the first and second neighboring support arms being combined or held together near or adjoining one another, the distal end part of the first support arm being combined or held together near or adjoining a distal end part of a neighboring support arm that is not the second support arm, the distal end part of the second support arm being combined or held together near or adjoining a distal end part of a neighboring support arm that is not the first support arm, each of the plurality of support arms in the electrode assembly being combined or held together at or near its distal end part with a neighboring support arm that is different from the neighboring support arm with which it is combined or held together at its proximal end part.

In yet another embodiment, there is provided a cardiac mapping catheter configured for electrophysiological mapping and suitable for intravascular insertion in a patient's heart comprising a flexible elongated body having a distal portion with a distal end and a proximal portion and an electrode assembly located at the distal portion, the electrode assembly comprising a plurality x of at least 4 support arms, each support arm having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition where the plurality of support arms is arranged in a collapsed bundle, and a second expanded condition where the plurality of support arms forms an expanded basket structure, wherein the plurality of support arms further comprises first and second neighboring support arms, the distal end parts of the first and second neighboring support arms being combined or held together near or adjoining one another, the proximal end part of the first support arm being combined or held together near or adjoining a proximal end part of a neighboring support arm that is not the second support arm, the proximal end part of the second support arm being combined or held together near or adjoining a proximal end part of a neighboring support arm that is not the first support arm, each of the plurality of support arms in the electrode assembly being combined or held together at or near its proximal end part with a neighboring support arm that is different from the neighboring support arm with which it is combined or held together at its distal end part.

In still another embodiment, there is provided cardiac mapping catheter configured for electrophysiological mapping and suitable for intravascular insertion in a patient's heart comprising a flexible elongated body having a distal portion with a distal end and a proximal portion and an electrode assembly located at the distal portion, the electrode assembly comprising a plurality x of at least 4 support arms, each support arm having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition where the plurality of support arms is arranged in a collapsed bundle, and a second expanded condition where the plurality of support arms forms an expanded basket structure, wherein the basket structure comprises two pole areas P1 and P2 that lie along a basket axis A, in the expanded condition each of the support arms spans a curve of about 180° between the two pole areas P1 and P2, an angle $\alpha$ defines a circumferential distance along a support arm from at least one of the poles P1 and P2 to a boundary between at least one of the proximal and distal end parts of the support arm and the central or main part of the support arm, the angle $\alpha$ ranges between about 5° and about 40°, and no electrodes are disposed along the circumferential distance or distances defined by the angle $\alpha$.

In another embodiment, there is provided a cardiac mapping catheter configured for electrophysiological mapping and suitable for intravascular insertion in a patient's heart comprising a flexible elongated body having a distal portion with a distal end and a proximal portion and an electrode assembly located at the distal portion, the electrode assembly comprising a plurality x of at least 4 support arms, each support arm having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition where the plurality of support arms is arranged in a collapsed bundle, and a second expanded condition where the plurality of support arms forms an expanded basket structure, wherein the proximal end part of each support arm is combined or held near or together with the proximal end part of a neighboring support arm, and the distal end part of each support member is combined or held near or together with the distal end part of a support arm that is not the neighboring support arm.

In yet another embodiment, there is provided a cardiac mapping catheter configured for electrophysiological mapping and suitable for intravascular insertion in a patient's heart comprising a flexible elongated body having a distal portion with a distal end and a proximal portion and an electrode assembly located at the distal portion, the electrode assembly comprising a plurality x of at least 4 support arms, each support arm having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition where the plurality of support arms is arranged in a collapsed bundle, and a second expanded condition where the plurality of support arms forms an expanded basket structure, wherein the distal end part of each support arm is combined or held near or together with the distal end part of a neighboring support arm, and the proximal end part of each support member is combined or held near or together with the proximal end part of a support arm that is not the neighboring support arm.

In still another embodiment, there is provided a cardiac mapping catheter configured for electrophysiological mapping and suitable for intravascular insertion in a patient's heart comprising a flexible elongated body having a distal portion with a distal end and a proximal portion, and an electrode assembly located at the distal portion, the electrode assembly comprising a plurality x of at least 4 support arms, each support arm having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition where the plurality of support arms is arranged in a collapsed bundle, and a second expanded condition where the plurality of support arms forms an expanded basket structure, at least one of the distal end parts and the proximal end parts being combined or held together with combining means, wherein the support arms and combining means are together configured such that one support arm may be not be deflected or bent towards a neighboring support arm by an angle exceeding β when at least one of the arms is in contact with a surface, the angle β ranging between about 5° and about 30°.

Further embodiments are disclosed herein or will become apparent to those skilled in the art after having read and understood the claims, specification and drawings hereof.

BRIEF DESCRIPTION OF THE DRAWINGS

Different aspects of the various embodiments will become apparent from the following specification, drawings and claims in which:

FIG. 4a is an enlarged view of an area of the electrode assembly of the elongated medical device of FIG. 3a according to the marking IVa in FIG. 3a;

The drawings are not necessarily to scale. Like numbers refer to like parts or steps throughout the drawings.

DETAILED DESCRIPTIONS OF SOME EMBODIMENTS

Described herein are various embodiments of a cardiac mapping catheter, and associated components, systems and methods of making and using same.

Systems and methods configured to detect in a patient's heart a location of a source of at least one cardiac rhythm disorder are disclosed herein. In the following description, for the purposes of explanation, numerous specific details are set forth in order to provide a thorough understanding of example embodiments or aspects. It will be evident, however, to one skilled in the art that an example embodiment may be practiced without necessarily using all of the disclosed specific details.

In one embodiment, an elongated medical device is provided that is suitable for intravascular insertion, such as a catheter for exploration or treatment of a vessel, organ or other body cavity which includes an electrode assembly for electrophysiological mapping of cardiac or vessel areas or the like medical apparatus. The electrode assembly may be used to map circular excitation patterns (rotors), e.g., of the left atrium of the heart.

Figure 1:
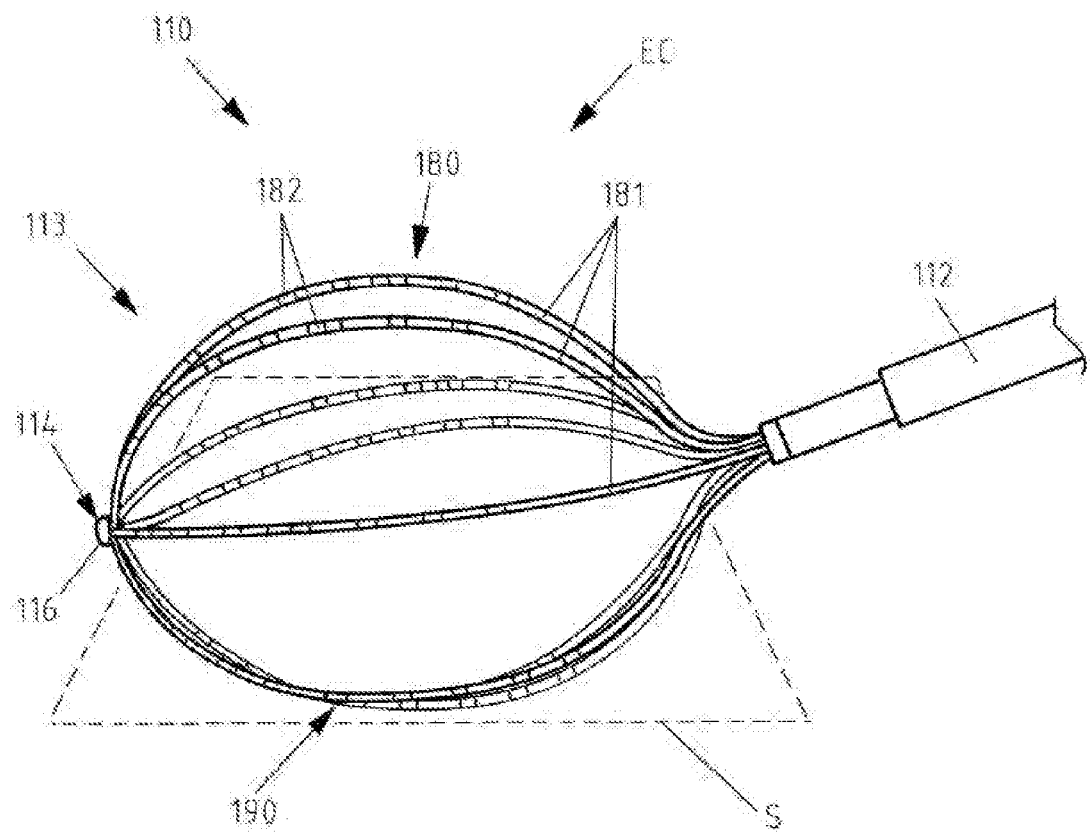
FIG. 1 is a schematic view of a basket type electrophysiological mapping catheter according to the prior art with an electrode assembly comprising support arms, the electrode assembly being in an expanded condition with a part of the support arms touching a surface.

Referring now to FIG. 1, there is illustrated a prior art elongated medical device 110 which is formed as a mapping catheter. The elongated medical device 110 comprises an elongated body 112, only a distal portion 113 of which is shown in FIG. 1. The elongated medical device 110/mapping catheter comprises a basket type electrode assembly 180 that is displayed in FIG. 1 in its expanded condition (EC). The electrode assembly 180 comprises eight support arms 181 that carry electrodes 182. In the example shown, there are eight electrodes 182 arranged on each of the eight support arms 181. A tip 116 is disposed at a distal end 114 of the distal portion 113 of the elongated medical device 110. FIG. 1 depicts the situation where the basket type electrode assembly 180 with its support arms 181 touches a surface S, e.g., an organ or body surface such as a patient's endocardium. As can be seen, the support arms 181 in contact with surface S bunch or accumulate on the surface S, and form a cluster 190 such that the 24 electrodes of the affected three support arms 181 effectively act, by way of example, as only 8 electrodes, as in the example of FIG. 1 the 24 electrodes of the three support arms are bunched together to form eight clusters, each cluster having three electrodes associated therewith. Due to such clustering, the spatial resolution of the electrodes is reduced significantly.

Figure 2:
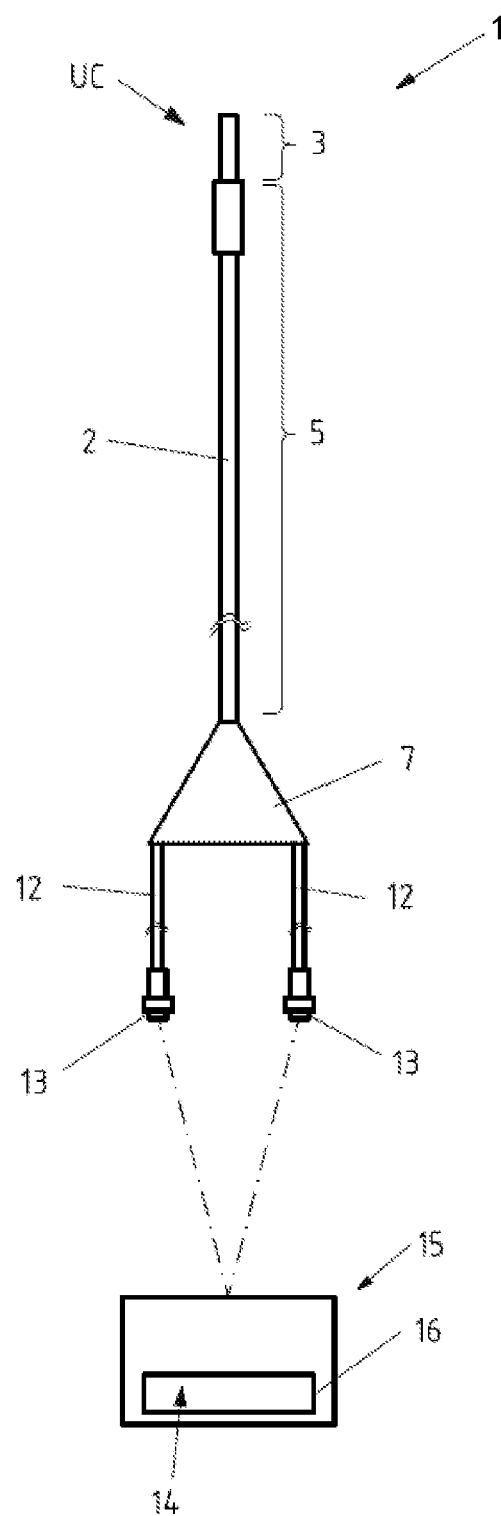
FIG. 2 is a schematic view of an electrophysiological mapping system comprising an elongated medical device for exploration or treatment of a vessel or organ or other body cavity, having an electrode assembly for electrophysiological mapping of cardiac or vessel areas, the electrode assembly being in a first, retracted condition, and a data processing and control unit/and a data output unit.
Figure 3A:
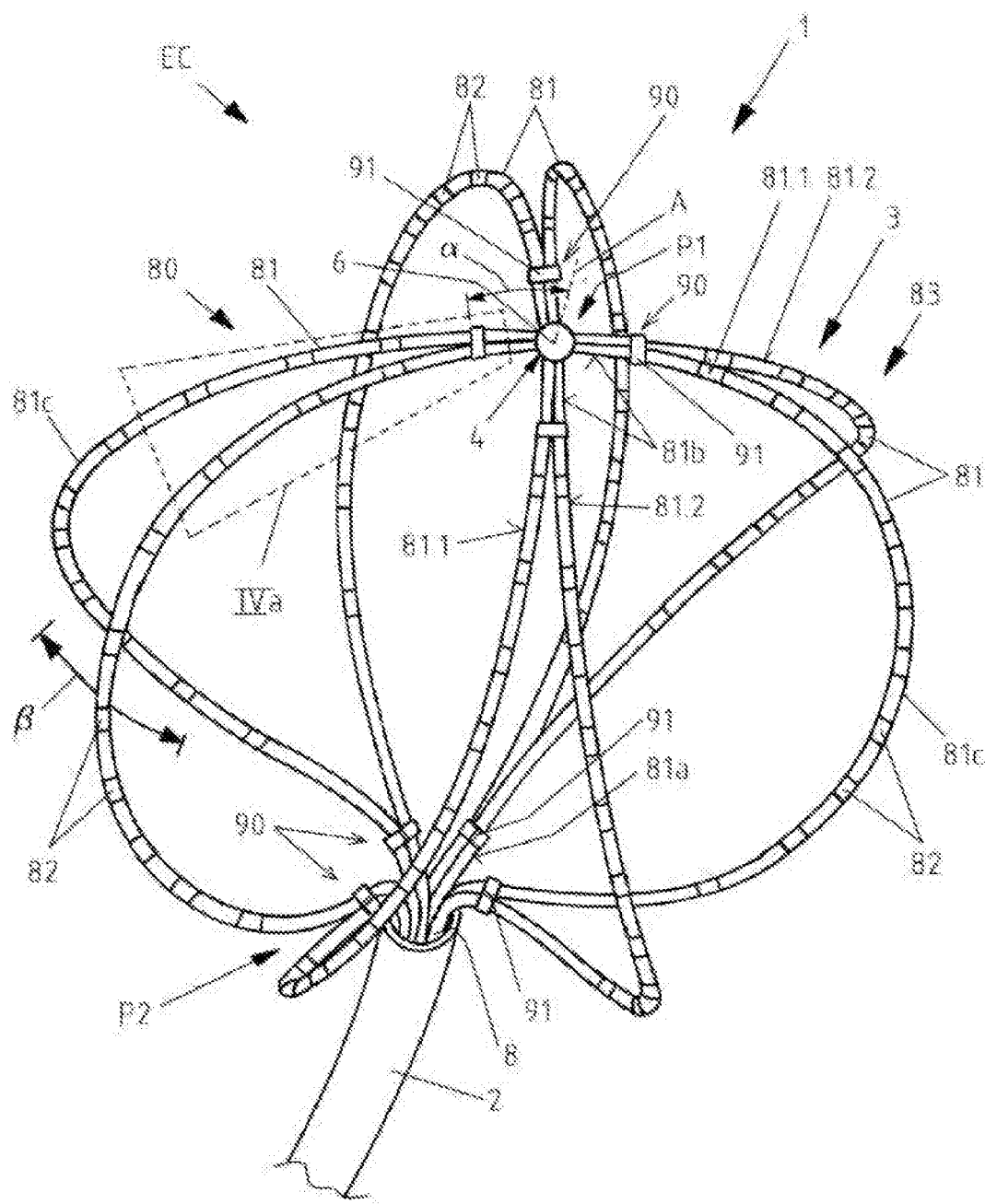
FIG. 3a is a perspective view on a distal portion of the elongated medical device according to FIG. 2 in a second, expanded condition of the electrode assembly.

Referring to FIGS. 2, 3a, 4a and 5a, there is shown an elongated medical device 1 formed as mapping catheter. The elongated medical device 1 comprises an elongated body 2, comprising a distal portion 3 and a proximal portion 5. At the distal portion 3 of the elongated medical device 1, a tip 6 is arranged at the distal end 4 of the device as shown in FIG. 3a. The elongated medical device 1 further comprises an electrode assembly 80/mapping electrode assembly 80 that is located at the distal portion 3 and comprises in the embodiment of FIGS. 2 and 3a a plurality x of eight support arms 81 (or splines), where at least four (x=4) of such support arms 81 are provided. Each support arm 81 has a proximal end part 81a, a distal end part 81b and a main part 81c located between the proximal end part 81a and the distal end part 81b. The eight support arms 81 are connected to the tip 6 at their respective distal end parts 81b. Note that even and odd numbers of support arms 81 are contemplated, such as by way of non-limiting example 4, 5, 6, 7, 8, 9, 10, 11, 12, 13, 14, 15 and 16 support arms 81.

The central part 81c of each support arm 81 carries a plurality of electrodes 82 (also referred to as mapping electrodes), which according to one embodiment may comprise gold or gold plating for enhanced electro-conductivity; other suitable electrically conductive and biocompatible metals and metal alloys for the electrodes are also contemplated, such as platinum, titanium, niobium, tantalum, and/or alloys or mixtures thereof. In one embodiment ten electrodes 82 are disposed on each support arm. In some embodiments, and by way of non-limiting example, the surface area an electrode 82 may range between about 0.01 $mm^2$ and about 0.25 $mm^2$.

A basket structure electrode assembly 80 may be formed using conventional wire, braided twisted or stranded electrical conductors and conventional electrodes. Common techniques for operably connecting metal electrodes to their corresponding wire electrical conductors in medical electrical leads include welding, swaging, crimping and staking. Likewise, the flexible elongated body 2 of the catheter may comprise a polymeric coating or material such as silicone, polyurethane or any other suitable polymeric material. Indeed, in one embodiment catheter 1 is formed and manufactured using largely conventional manufacturing methods and materials, where lead body 2 is formed using well-known biocompatible polymeric materials that sheath or overlie internally disposed flexible electrical conductors (e.g., braided, stranded, and/or twisted wires) that are electrically connected at their distal ends to the electrodes disposed on the support arms, and the support arms themselves are formed from similar or the same biocompatible polymeric materials, flexible electrical conductors, and metal or metal alloy electrodes.

At the proximal end of the elongated medical device 1, a handle 7 or other manipulable control device may be attached to the proximal portion 5. The handle 7 may be used to manually control expansion or retraction of the electrode assembly 80 using, by way of non-limiting example, an internal pull wire operably connected to a proximal end of the support arms. When the internal pull wire is pushed in a distal direction, the support arms assume an expanded condition to form the basket structure. When the internal pull wire is pulled in a proximal direction, the support arms assume a retracted condition inside the catheter body 2.

The electrode assembly 80 in FIG. 2 is shown in its first condition UC (unexpanded condition), where the electrode assembly 80 is stored internally in space 8 within the tubular elongated body 2 of the elongated medical device 1. In this stored position the plurality of at least x=4 support arms 81 forms a dense collapsed bundle. In the first condition UC the elongated medical device 1/catheter may be introduced into a vessel, organ or other body cavity by, for example, intravascular means.

In FIG. 3a the electrode assembly 80 is in its second condition EC (expanded condition) in which the support arms 81 project away from the elongated body 2 to form a basket type structure 83. In this second expanded condition EC the device is deployed to collect electrophysiological data, i.e., for electrophysiological mapping.

As can be seen in FIG. 3a, the basket structure 83 with the support arms 81 has two pole areas P1, P2, which define a basket axis A. Between the two poles or pole areas P1, P2 each of the support arms 81 spans a curve or bow of about 180°. As shown in FIG. 3a, and in one embodiment, an angle α defines a circumferential distance along two support arms that have been combined or held together between axis A and the combining means 90 associated with the two such support arms. According to the embodiment that is employed, the angle α is not limited to circumferential distances defined by basket axis A and combining means 90, however, and can extend beyond combining means 90 or terminate prior to reaching combining means 90. In some embodiments, the circumferential distance defined by angle α delineates or approximately delineates the border or boundary between the respective proximal end parts 81a/distal end parts 81b and the central or main parts 81c disposed along the curve or bow defined by the pertinent support arms 81. In some embodiments, the angle α ranges between about 5° and about 40°, between about 5° and about 30°, between about 5° and about 25°, between about 5° and about 20°, between about 5° and about 15°, and between about 5° and about 10°. In the embodiment of FIG. 3a, angle α is about 15°.

It should be mentioned that the number of electrodes on the support arm may be varied such that in a pair of neighboring support arms one support arm carries more electrodes than the other one. For example, one support arm may carry twelve electrodes while a neighboring support arm carries eight electrodes. With such varying numbers of electrodes, the number of electrodes in the equator area or central portion of the basket structure can be enhanced, while the number of electrodes towards the "poles" (which often produce the least useful information) may be reduced.

For example, when the electrodes 82 are disposed in the central or main part 81c of each support arm and not in the proximal end part 81 and/or the distal end part 81b of such support arm, and in the case where the angle α delineates or approximately delineates the border or boundary between such proximal end part 81a, distal end part 81b, and the central or main part 81c, electrodes 82 can be configured such that they are disposed along such proximal end part 81a or distal end part 81b, and the angle α can be employed to define where electrodes are not to be found on the support arms. In such a case, the greater the angle α, the greater the circumferential distance to poles P1 or P2 from the nearest electrode 82. Such an electrode configuration can result in enhanced sensing and spatial resolution since electrodes are not being "wasted" due to their undesired proximity to the poles P1 and P2.

Figure 4A:
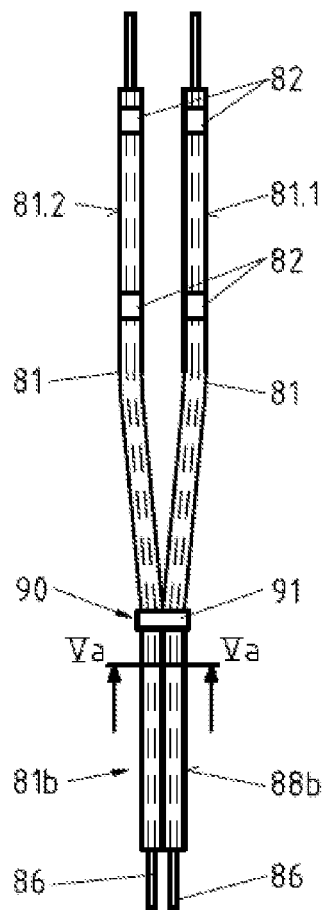
Figure 5A:
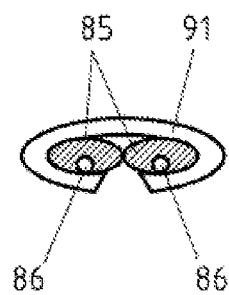
FIG. 5a is an enlarged cut section through a pair of neighboring support arms according to the marking Va in FIG. 4a, and FIG. 5b is an enlarged cut section through a pair of neighboring support arms analog to FIG. 5a according to a further embodiment of an elongated medical device.

Referring to FIGS. 3a, 4a and 5a, the plurality x of eight support arms 81 is shown to comprise pairs of neighboring support arms 81.1, 81.2. In one embodiment, all first and second neighboring support arms 81.1, 81.2 are combined by combining means 90 at their proximal end parts 81a to form united end parts 88a, so that all pairs of neighboring support arms 81.1, 81.2 are united at their proximal end parts 81a.

Further, and in one embodiment, all second and first neighboring support arms 81.2, 81.1 are combined by combining means 90 at their distal end parts 81b, to form united end parts 88*b*, such that all pairs of neighboring support arms 81.2, 81.1 are united at their distal end parts 81*b*. As shown in FIG. 3*a*, each support arm 81 is combined at its distal end part 81*b* with a neighboring support arm 81 that is different from the neighboring support arm to which it is combined or attached at its proximal end part 81*a*, which forms a mechanically stabilized framework that is configured to prevent or impede the undesired clustering of electrodes in only a few locations along the patient's endocardial wall or surface. Instead, the stabilized framework of support arms results in electrodes being much more evenly and regularly spaced and positioned along the patient's endocardial wall or surface during an EP mapping procedure.

As shown in the Figures, a modification in combining neighboring support arms 81.1, 81.2 may be employed, which besides forming united end parts 88*a*, 88*b*, further stabilizes the basket structure 83 of the electrode assembly 80. As a result, and in one embodiment, the central part 81*c* of an individual support arm 81 has a limited maximum angle β under which it may be deflected or bent towards a neighboring support arm when touching a surface. In one embodiment, this result is achieved at least in part by appropriate configuration of combining means 90 with respect to the two support arms 81 to which combining means 90 is attached. That is, combining means 90 located at one or both ends of a given support arm 81 are configured to constrain the lateral movement of one support arm towards or in the direction of an adjoining or neighboring support arm. In one embodiment, the maximum angle β of deflection is approximately $\pm(360°/2x)$, with x being the number of support arms 81. In another embodiment, this maximum possible angle β of deflection/freedom to be bent is less than $\pm((360°/x)-(360°/10))$, with x being the number of support arms 81. Many values for angle β are contemplated, such as angle β being about 5°, about 10°, about 15°, about 20°, about 22.5°, about 25°, about 30°, and/or about 35°. Ranges of angle β are also contemplated, such as between about 5° and about 35°, between about 5° and about 30°, between about 10° and about 30°, and between about 10° and about 25°, and between about 10° and about 20°. Other ranges and values of angle β are also contemplated. As a further result, in use of the medical device, the resulting electrode distribution of the basket structure 83 when in contact with surface S is more uniform than in the prior art (where support arms tend to bunch or cluster together). In one embodiment, united end portions 88*a*, 88*b* may be formed in basket-type electrode assemblies 80 having an even number (number divisible by 2) of support arms 81.

The combining means 90 are preferably arranged on the border between the respective proximal end parts 81*a*/distal end parts 81*b* and the central parts 81*c*. In case of an adhesive or welded combining means 90, the combining means 90 may extend between this border and the pole area along a part of the length of the neighboring proximal and/or distal end parts 81*a*, 81*b* of the support arms 81 or over the entire length of the neighboring proximal and/or distal end parts 81*a*, 81*b*.

In the embodiment of FIGS. 3*a*, 4*a*, 5*a* the combining means 90 are formed as clamping elements or clamps 91. By means of the clamping elements 91 the distal end parts 81*b* and the proximal end parts 81*a* of neighboring support arms 81.1, 81.2 are clamped together in tight fit. Such clamps or clamping elements 91 may easily be applied to a basket type catheter even after the electrode assembly 80 has been mounted at the elongated medical device 1. A retrofitting of basket type catheters with combining means 90 is accordingly possible and such retrofitted catheters are also within the scope of what is described and disclosed herein.

Figure 4B:
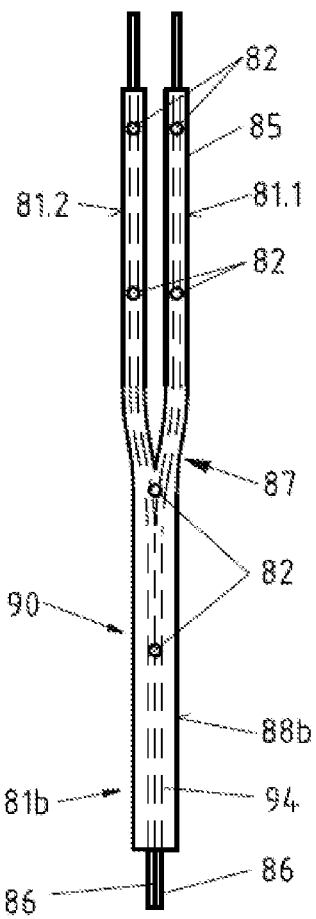
FIG. 4b is an enlarged view of an area of the electrode assembly of the elongated medical device of FIG. 3b according to the marking IVb in FIG. 3b.
Figure 4C:
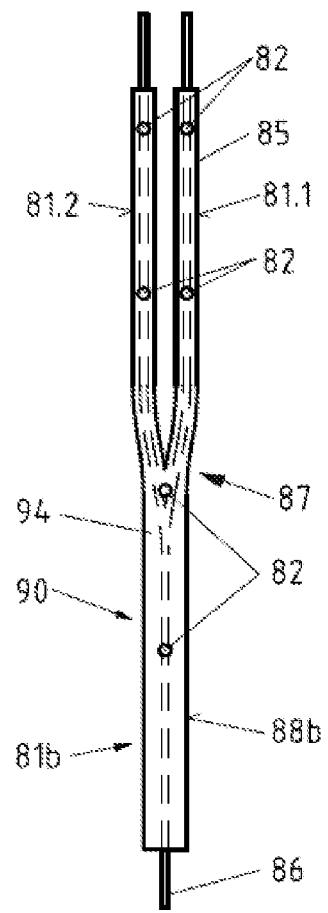
FIG. 4c is an enlarged view of an area of an electrode assembly of a further embodiment of an elongated medical device.
Figure 4D:
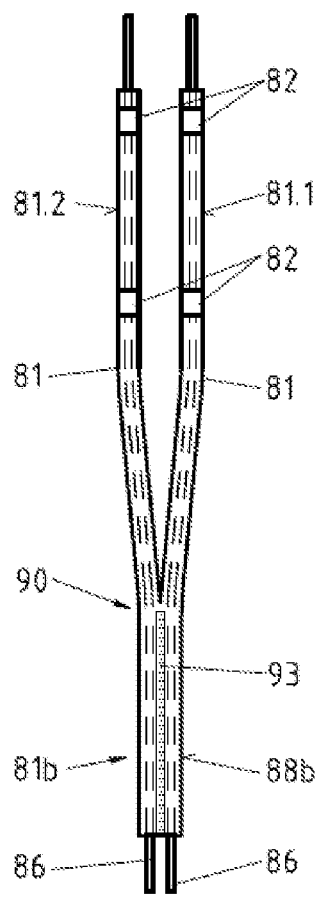
FIG. 4d is an enlarged view of an area of an electrode assembly of a further embodiment of an elongated medical device.
Figure 5B:
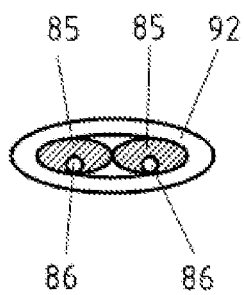

Some embodiments of alternative combining means 90 are displayed in FIGS. 4*d* and 5*b*. Many other types of combining structures and/or means are contemplated, however, including one or more polymeric layers, covers, sheaths, overmoldings, tubing, shrink tubing, clamps, ring members, rings, adhesives, lugs, welds, stakes, crimps, other suitable means or structures, or any combination or plurality thereof.

In the embodiment shown in FIG. 4*d*, the distal end parts 81*b* of neighboring support arms 81.1, 81.2 and the proximal end parts 81*a* of neighboring support arms 81.1, 81.2 are combined to form united end parts 88*a*, 88*b* by means of a joint 93 formed using an adhesive. The adhesive of joint 93 may be applied to portions or over almost the entire length of the united end parts 88*a*, 88*b*. Alternatively, a welded joint or welded connection may also be used to form joint 93.

In the embodiment shown in FIG. 5*b*, the distal end parts 81*b* of neighboring support arms 81.1, 81.2 and the proximal end parts 81*a* of neighboring support arms 81.1, 81.2 are combined to united end parts 88*a*, 88*b* by means of ring members or rings 92 instead of clamping elements. Clamping means of different types may also be used in combination.

Further, instead of ring member 92, a tube or shrink tube (not shown in the Figures), e.g., made of a polymeric material, may be used which may encompass or extend over the united proximal and distal end parts 81*a*, 81*b* over a part of their length or over their entire length and combine them to form the united end parts 88*a*, 88*b*.

Combining means 90, especially in embodiments where clamps or clamping elements 91 or ring members 92 are used, may also function as mapping electrodes. The combining means 90, formed of an electrically conductive metal, is electrically connected to electrical conductors or lines disposed in or on the support arms 81. The number of mapping electrodes may accordingly be augmented or enhanced.

Referring again to FIG. 4*a*, in one embodiment each of support arms 81 comprises a strand 86 formed of a shape memory metal and a PCB (printed circuit board) layer 85, where the PCB layers 85 carry the electrodes 82 and electrical conductors (not visible in the Figures) for operative connection to electrodes 82. The PCB layers 85 at least partially surround the strands 86, which in one embodiment may be formed as Nitinol wires of 0.1-0.3 mm diameter, preferentially 0.2 mm diameter. Other suitable metals or metal alloys may also be employed to form such strands, wires or electrical conductors.

Referring again to FIGS. 2 and 3*a*, the electrode assembly 80 is connected via connection 12 with a data processing and control unit 15, which energizes and controls the electrodes 82. Data processing and control unit 15 processes electrode mapping data from the electrode assembly 80 and outputs mapping data on a data output screen 14 of a data output unit 16. Connection 12 may be a cable, ribbon cable, flat conductor, flat flexible cable or any other suitable electrical connection. At the end of connection or line 12 there are connectors 13 located for connecting the elongated medical device 1 and its electrode assembly 80 and associated electronics to the data processing and control unit 15.

In one embodiment, the data processing and control unit 15 may comprise a suitably programmed and configured computing device such as a personal computer. Elongated medical device 1 may form a portion of a catheter system interfaced to a computing device. In respect to the electrophysiological mapping data, in one embodiment the data processing and control unit 15 is configured to process analog and/or digitized electrode measurement data and to output data for visualizing circular excitation pattern (rotors), e.g., in the left atrium of a patient's heart on a data output screen 14 of a data output unit 16.

In operation of the medical device 1, the medical device 1 or catheter is inserted in the patient's vessel, organ or other body cavity until it reaches the target area, which in one example is the left atrium of a patient's heart, or any other portion of the heart. Upon arrival in the target area the operator may expand the electrode assembly 80 by manipulating the handle 7. In this expanded condition EC of the electrode assembly 80 and its support arms 81 the medical device 1 will be pushed with its distal end 4 against body tissue and electrophysiological mapping may be initiated automatically or by the health care provider. Data analysis of electrophysiological data, such as action potential data, is performed on the data processing and control unit 15 respectively on a suitably programmed computing device.

Figure 3B:
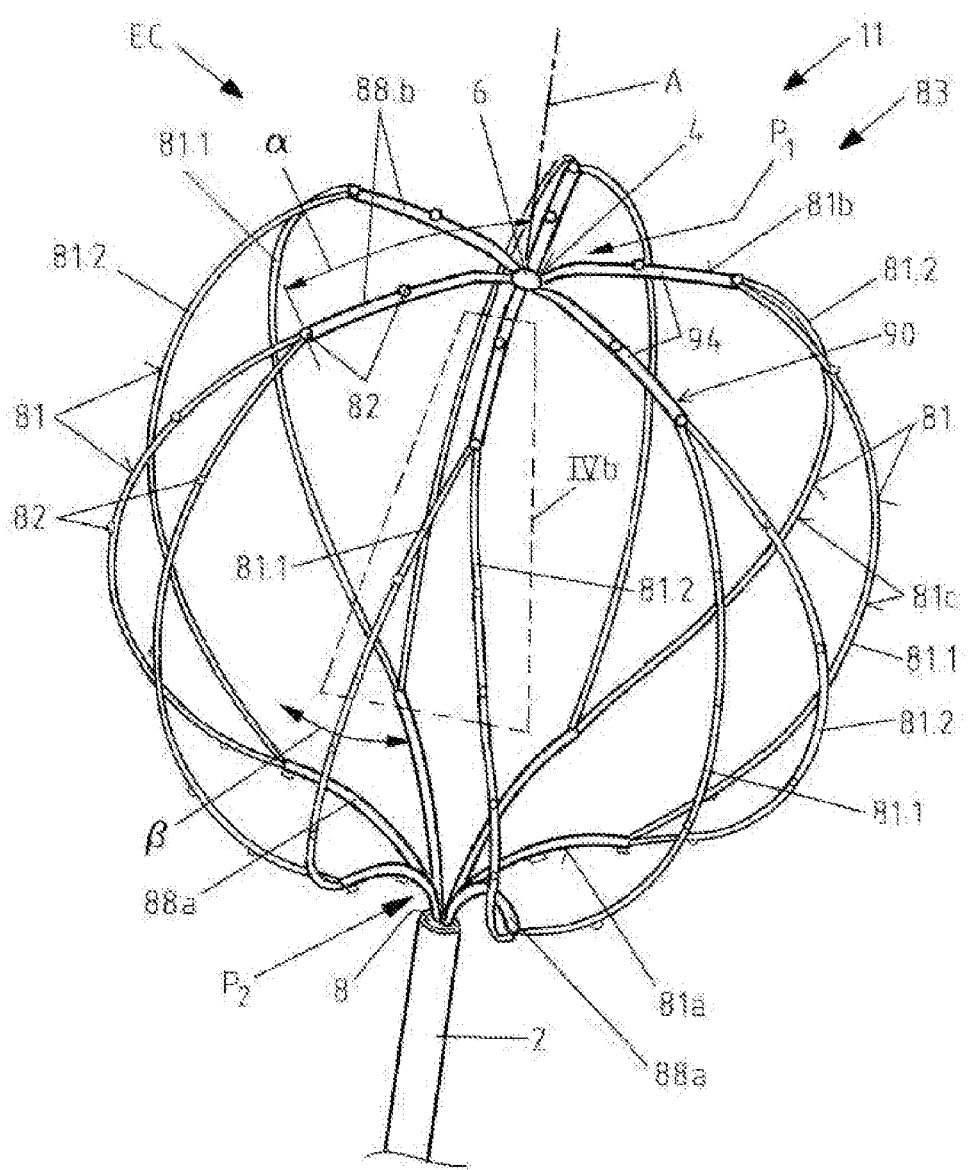
FIG. 3b is a perspective view on the distal portion of an elongated medical device in a further embodiment in the second, expanded condition of the electrode assembly.

FIGS. 3b and 4b display a further embodiment of the elongated medical device 11. For reference numerals and functions not described in the following text, reference is made to the descriptions of FIGS. 2, 3a, 4a and 5a. Similar parts are indicated with similar reference numerals. The embodiments shown in FIGS. 3b and 4b differ from those described with respect to FIGS. 2, 3a, 4a and 5a in that the combining means 90 are realized in the form of a flexible electrical polymeric substrate or sheet 94 disposed at the united end parts 88a, 88b of the neighboring support arms 81.1, 81.2. Flexible electrical polymeric substrate or sheet 94 comprises electrical conductors, which in one embodiment are made using thin film electrical conductor deposition techniques. In some embodiments, the thin film electrical conductors and their corresponding electrodes may be formed or deposited on a material chosen from the group of Mylar, Kevlar, polyimide, PEEK, an electrically conductive polyester, or other suitable flexible biocompatible materials. Flexible electrical polymeric substrate or sheet 94 may also, e.g., be formed as a PCB layer or an electro-ceramic layer. Further, and in the embodiments shown in FIGS. 3b and 4b, two electrodes 82 are disposed on each united end part 88a, 88b of the support arms 81, while four electrodes 82 are located on each central part 81c of the support arms 81.

The angle α defining the circumferential distance between the respective pole P1 or P2 and the border between the respective proximal end parts 81a/distal end parts 81b and the central parts 81c on this curve or bow is about 40° in this embodiment. Accordingly, a split point 87 (indicated in FIG. 4b) which lies in the border between the respective proximal end parts 81a/distal end parts 81b and the central parts 81c is in the same circumferential distance as defined by angle α of about 40°.

FIG. 4c displays a further embodiment of the elongated medical device similar to the embodiment of FIGS. 3b and 4b, but with modified support arms 81. For reference numerals and functions not described in the following text, reference is made to the descriptions of FIGS. 2, 3a, 3b, 4a, 4b and 5a. Similar parts are indicated with similar reference numerals. The embodiment of FIG. 4c differs from that of FIGS. 3b and 4b in that there is only one shape memory strand 86 in the united end parts 88a, 88b, whereas there are two strands 86 in the embodiment of FIGS. 3b and 4b.

At the split point 87, the single strand 86 splits into two strands 86, one in each neigh-boring support arm 81.1, 81.2. Single strand 86 may be welded in split point 87 with the two strands 86 of the neighboring support arms 81.1, 81.2.

Note that the various embodiments include those described above in the Summary, where, for example: (a) the attachment of distal and proximal end parts in neighboring support arms is reversed; (b) one end of a support arm need not be attached to a neighboring support arm (but only to a support arm that is not the same as that to which the support arm is attached or combined at another end); (c) where the angle α along a support arm is constrained between certain angular limits and no electrodes are disposed on a support arm within the range of angle α, and (d) where the maximum angle β over which one support arm may be deflected towards a neighboring support arm when at least one of the arms is in contact with a surface such a patient's endocardium is constrained within certain angular limits.

The various systems, devices, components and methods described and disclosed herein may also be adapted and configured for use in electrophysiological mapping applications other than those involving the interior of a patient's heart. These alternative applications include EP mapping and diagnosis of a patient's epicardium, a patient's spinal cord or other nerves, or a patient's brain or portions thereof.

In addition, the cardiac mapping catheter described and disclosed herein may be modified to include a cardiac ablation device at or near distal end 114 or tip 116. Such ablation devices may include, but are not limited to RF, cryogenic, and radioactive ablation devices. The cardiac mapping catheter may also include a force sensor, temperature sensor and/or irrigation device disposed near or at its tip 116. Moreover, the various embodiments described and disclosed herein include methods of making and using same, as described, for example, in the Summary above.

Additional embodiments can include the following elements and features:

Embodiment A

A cardiac mapping catheter configured for electrophysiological mapping and suitable for intravascular insertion in a patient's heart, comprising a flexible elongated body having a distal portion with a distal end and a proximal portion, and an electrode assembly located at the distal portion, the electrode assembly comprising a plurality x of at least 4 support arms, each support arm having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition where the plurality of support arms is arranged in a collapsed bundle, and a second expanded condition where the plurality of support arms forms an expanded basket structure, wherein the plurality of support arms further comprises first and second neighboring support arms, the proximal end parts of the first and second neighboring support arms being combined or held together near or adjoining one another, the distal end part of the first support arm being combined or held together near or adjoining a distal end part of a neighboring support arm that is not the second support arm, the distal end part of the second support arm being combined or held together near or adjoining a distal end part of a neighboring support arm that is not the first support arm, each of the plurality of support arms in the electrode assembly being combined or held together at or near its distal end part with a neighboring support arm that is different from the neighboring support arm with which it is combined or held together at its proximal end part.

Embodiment A, and other embodiments, may include one or more of the following elements or features: x is evenly divisible by the number 2; at least one of the distal end parts and the proximal end parts are combined or held together with combining means; the support arms and combining means are together configured such that one support arm cannot be deflected or bent towards a neighboring support arm by an angle exceeding β when at least one of the arms is in contact with a surface, the angle β ranging between about 5° and about 30°; the combining means comprises one or more of a polymeric layer, a cover, a sheath, overmolding, tubing, shrink tubing, a clamp, a ring member, an adhesive joint, a lug, a weld, a stake, a crimp, or any combination of the foregoing; at least some of the combining means comprise an electrically conductive metal or metal alloy forming one or more electrodes, and such electrodes are electrically connected to electrical conductors disposed in one or more of the support arms; at least one of the support arms comprises a flexible electrical polymeric sheet comprising electrodes; the number x of support arms equals 4, 6, 8, 10 or 12; the number of electrodes disposed on each support arm ranges between 4 electrodes and 24 electrodes; the plurality of electrodes disposed on each support arm is distributed spatially substantially evenly thereon; the basket structure comprises two pole areas P1 and P2 that lie along a basket axis A; in the expanded condition each of the support arms spans a curve of about 180° between the two pole areas P1 and P2; an angle α defines a circumferential distance along a support arm from at least one of the poles P1 and P2 to a boundary between at least one of the proximal and distal end parts of the support arm and the central or main part of the support arm, the angle α ranges between about 5° and about 40°, and no electrodes are disposed along the circumferential distance or distances defined by the angle α; the angle α ranges between about 5° and about 30°; the angle α ranges between about 10° and about 25°; and braided, twisted or stranded electrical conductors operatively connected to the electrodes; at least portions of the flexible elongated body comprise an electrically insulative polymeric material.

Embodiment B

A method of making a cardiac mapping catheter configured for electrophysiological mapping and suitable for intravascular insertion in a patient's heart, the method comprising forming a flexible elongated body having a distal portion with a distal end and a proximal portion, and forming an electrode assembly configured to be located at or near the distal portion, the electrode assembly comprising a plurality x of at least 4 support arms, each support arm having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition where the plurality of support arms is arranged in a collapsed bundle, and a second expanded condition where the plurality of support arms forms an expanded basket structure; wherein the plurality of support arms further comprises first and second neighboring support arms, the proximal end parts of the first and second neighboring support arms being combined or held together near or adjoining one another, the distal end part of the first support arm being combined or held together near or adjoining a distal end part of a neighboring support arm that is not the second support arm, the distal end part of the second support arm being combined or held together near or adjoining a distal end part of a neighboring support arm that is not the first support arm, each of the plurality of support arms in the electrode assembly being combined or held together at or near its distal end part with a neighboring support arm that is different from the neighboring support arm with which it is combined or held together at its proximal end part.

Embodiment B, and other embodiments, may include one or more of the following elements, features or steps: x is evenly divisible by the number 2; combining or holding together the distal end parts or proximal end parts with combining means; one or more of a polymeric layer, a cover, a sheath, overmolding, tubing, shrink tubing, a clamp, a ring member, an adhesive joint, a lug, a weld, a stake, a crimp, or any combination of the foregoing; the support arms are formed using a flexible electrical polymeric sheet; an angle α defines a circumferential distance along a support arm from at least one of the poles P1 and P2 to a boundary between at least one of the proximal and distal end parts of the support arm and the central or main part of the support arm, the angle α ranges between about 5° and about 40°, and no electrodes are disposed along the circumferential distance or distances defined by the angle α; the angle α ranges between about 5° and about 30°; the angle α ranges between about 10° and about 25°; operatively connecting braided, twisted or stranded electrical conductors to the electrodes; and forming at least portions of the flexible elongated body with an electrically insulative polymeric material.

Embodiment C

A cardiac mapping catheter configured for electrophysiological mapping and suitable for intravascular insertion in a patient's heart, comprising a flexible elongated body having a distal portion with a distal end and a proximal portion, and an electrode assembly located at the distal portion, the electrode assembly comprising a plurality x of at least 4 support arms, each support arm having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition where the plurality of support arms is arranged in a collapsed bundle, and a second expanded condition where the plurality of support arms forms an expanded basket structure, wherein the plurality of support arms further comprises first and second neighboring support arms, the distal end parts of the first and second neighboring support arms being combined or held together near or adjoining one another, the proximal end part of the first support arm being combined or held together near or adjoining a proximal end part of a neighboring support arm that is not the second support arm, the proximal end part of the second support arm being combined or held together near or adjoining a proximal end part of a neighboring support arm that is not the first support arm, each of the plurality of support arms in the electrode assembly being combined or held together at or near its proximal end part with a neighboring support arm that is different from the neighboring support arm with which it is combined or held together at its distal end part.

Embodiment C, and other embodiments, may include one or more of the following elements or features: x is evenly divisible by the number 2.

Embodiment D

A cardiac mapping catheter configured for electrophysiological mapping and suitable for intravascular insertion in a patient's heart, comprising a flexible elongated body having a distal portion with a distal end and a proximal portion, and an electrode assembly located at the distal portion, the electrode assembly comprising a plurality x of at least 4 support arms, each support arm having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition where the plurality of support arms is arranged in a collapsed bundle, and a second expanded condition where the plurality of support arms forms an expanded basket structure; wherein the basket structure comprises two pole areas P1 and P2 that lie along a basket axis A, in the expanded condition each of the support arms spans a curve of about 180° between the two pole areas P1 and P2, an angle α defines a circumferential distance along a support arm from at least one of the poles P1 and P2 to a boundary between at least one of the proximal and distal end parts of the support arm and the central or main part of the support arm, the angle α ranges between about 5° and about 40°, and no electrodes are disposed along the circumferential distance or distances defined by the angle α.

Embodiment E

A cardiac mapping catheter configured for electrophysiological mapping and suitable for intravascular insertion in a patient's heart, comprising a flexible elongated body having a distal portion with a distal end and a proximal portion, and an electrode assembly located at the distal portion, the electrode assembly comprising a plurality x of at least 4 support arms, each support arm having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition where the plurality of support arms is arranged in a collapsed bundle, and a second expanded condition where the plurality of support arms forms an expanded basket structure; wherein the proximal end part of each support arm is combined or held near or together with the proximal end part of a neighboring support arm, and the distal end part of each support member is combined or held near or together with the distal end part of a support arm that is not the neighboring support arm.

Embodiment F

A cardiac mapping catheter configured for electrophysiological mapping and suitable for intravascular insertion in a patient's heart, comprising a flexible elongated body having a distal portion with a distal end and a proximal portion, and an electrode assembly located at the distal portion, the electrode assembly comprising a plurality x of at least 4 support arms, each support arm having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition where the plurality of support arms is arranged in a collapsed bundle, and a second expanded condition where the plurality of support arms forms an expanded basket structure; wherein the distal end part of each support arm is combined or held near or together with the distal end part of a neighboring support arm, and the proximal end part of each support member is combined or held near or together with the proximal end part of a support arm that is not the neighboring support arm.

Embodiment G

A cardiac mapping catheter configured for electrophysiological mapping and suitable for intravascular insertion in a patient's heart, comprising a flexible elongated body having a distal portion with a distal end and a proximal portion, and an electrode assembly located at the distal portion, the electrode assembly comprising a plurality x of at least 4 support arms, each support arm having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition where the plurality of support arms is arranged in a collapsed bundle, and a second expanded condition where the plurality of support arms forms an expanded basket structure, at least one of the distal end parts and the proximal end parts being combined or held together with combining means, wherein the support arms and combining means are together configured such that one support arm may be not be deflected or bent towards a neighboring support arm by an angle exceeding β when at least one of the arms is in contact with a surface, the angle β ranging between about 5° and about 30°.

What have been described above are examples and embodiments of the devices and methods described and disclosed herein. It is, of course, not possible to describe every conceivable combination of components or methodologies for purposes of describing the invention, but one of ordinary skill in the art will recognize that many further combinations and permutations of the devices and methods described and disclosed herein are contemplated and possible. Accordingly, the devices and methods described and disclosed herein are intended to embrace all such alterations, modifications and variations that fall within the scope of the appended claims. In the claims, unless otherwise indicated, the article "a" is to refer to "one or more than one."

The foregoing outlines features of several embodiments so that those skilled in the art may better understand the detailed description set forth herein. Those skilled in the art will now understand that many different permutations, combinations and variations of elongated medical device 1 fall within the scope of the various embodiments. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

After having read and understood the present specification, those skilled in the art will now understand and appreciate that the various embodiments described herein provide solutions to long-standing problems, both in the use of electrophysiological mapping systems and in the use of cardiac ablation systems.

I claim:

1. A cardiac mapping catheter configured for electrophysiological mapping and suitable for intravascular insertion in a patient's heart, comprising:
    a flexible elongated body having a distal portion with a distal end and a proximal portion, and
    an electrode assembly located at the distal portion, the electrode assembly comprising a plurality x of at least 4 support arms, each support arm having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition where the plurality of support arms is arranged in a collapsed bundle, and a second expanded condition where the plurality of support arms forms an expanded basket structure;
        wherein the plurality of support arms further comprises first and second neighboring support arms, the proximal end parts of the first and second neighboring support arms being combined or held together to one another, the distal end part of the first support arm being combined or held together to a distal end part of a neighboring support arm that is not the second support arm, the distal end part of the second support arm being combined or held together to a distal end part of a neighboring support arm that is not the first support arm, each of the plurality of support arms in the electrode assembly being combined or held together at its distal end part with a neighboring support arm that is different from the neighboring support arm with which it is combined or held together at its proximal end part, and further wherein each of the plurality of support arms in the electrode assembly is not connect to, or combined or held together with, any of the other of the plurality of support arms along the main parts corresponding thereto.

2. The cardiac mapping electrode of claim 1, wherein x is evenly divisible by the number 2.

3. The cardiac mapping catheter of claim 1, wherein at least one of the distal end parts and the proximal end parts are combined or held together with combining means comprising one or more of a polymeric layer, a cover, a sheath, overmolding, tubing, shrink tubing, a clamp, a ring member, an adhesive joint, a lug, a weld, a stake, a crimp, or any combination of the forgoing.

4. The cardiac mapping catheter of claim 3, wherein the support arms and combining means are together configured such that one support arm cannot be deflected or bent towards a neighboring support arm by an angle exceeding β when at least one of the arms is in contact with a surface, the angle β ranging between about 5° and about 30°.

5. The cardiac mapping catheter of claim 3, wherein at least some of the combining means comprise an electrically conductive metal or metal alloy forming one or more electrodes, and such electrodes are electrically connected to electrical conductors disposed in one or more of the support arms.

6. The cardiac mapping catheter of claim 1, wherein at least one of the support arms comprises a flexible electrical polymeric sheet comprising electrodes.

7. The cardiac mapping catheter of claim 1, wherein the number x of support arms equals 4, 6, 8, 10 or 12.

8. The cardiac mapping catheter of claim 1, wherein the number of electrodes disposed on each support arm ranges between 4 electrodes and 24 electrodes.

9. The cardiac mapping catheter of claim 1, wherein the plurality of electrodes disposed on each support arm is distributed spatially evenly thereon.

10. The cardiac mapping catheter of claim 1, wherein the electrode assembly comprises two pole areas P1 and P2 that lie along a basket axis A.

11. The cardiac mapping catheter of claim 10, wherein in the expanded condition each of the support arms spans a curve of 180° between the two pole areas P1 and P2.

12. The cardiac mapping catheter of claim 10, wherein an angle α defines a circumferential distance along a support arm from at least one of the poles P1 and P2 to a boundary between at least one of the proximal and distal end parts of the support arm and the main part of the support arm, the angle α ranges between 5° and about 40°, and no electrodes are disposed along the circumferential distance or distances defined by the angle α.

13. The cardiac mapping catheter of claim 12, wherein the angle α ranges between 5° and 30°.

14. The cardiac mapping catheter of claim 12, wherein the angle α ranges between 10° and 25°.

15. The cardiac mapping catheter of claim 1, further comprising braided, twisted or stranded electrical conductors operatively connected to the electrodes.

16. The cardiac mapping catheter of claim 1, wherein at least portions of the flexible elongated body comprise an electrically insulative polymeric material.

17. A method of making a cardiac mapping catheter configured for electrophysiological mapping and suitable for intravascular insertion in a patient's heart, the method comprising:
    forming a flexible elongated body having a distal portion with a distal end and a proximal portion, and
    forming an electrode assembly configured to be located at or near the distal portion, the electrode assembly comprising a plurality x of at least 4 support arms, each support arm having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition where the plurality of support arms is arranged in a collapsed bundle, and a second expanded condition where the plurality of support arms forms an expanded basket structure;
    wherein the plurality of support arms further comprises first and second neighboring support arms, the proximal end parts of the first and second neighboring support arms being combined or held together to one another, the distal end part of the first support arm being combined or held together to a distal end part of a neighboring support arm that is not the second support arm, the distal end part of the second support arm being combined or held together to a distal end part of a neighboring support arm that is not the first support arm, each of the plurality of support arms in the electrode assembly being combined or held together at its distal end part with a neighboring support arm that is different from the neighboring support arm with which it is combined or held together at its proximal end part, and further wherein each of the plurality of support arms in the electrode assembly is not connected to, or combined or held together with, and of the other of the plurality of support arms along the main parts corresponding thereto.

18. The method of claim 17, wherein x is evenly divisible by the number 2.

19. The method of claim 17, further comprising combining or holding together the distal end parts or proximal end parts with combining means comprising one or more of a polymeric layer, a cover, a sheath, overmolding, tubing, shrink tubing, a clamp, a ring member, an adhesive joint, a lug, a weld, a stake, a crimp, or any combination of the foregoing.

\* \* \* \* \*